(12) United States Patent
Quan et al.

(10) Patent No.: US 9,593,158 B2
(45) Date of Patent: Mar. 14, 2017

(54) PROCESS FOR THE PREPARATION OF GELATIN

(71) Applicant: DSM IP ASSETS B.V., Heerlen (NL)

(72) Inventors: Zhong-Hua Quan, Shanghai (CN); Monica Diana Vlasie, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/427,659

(22) PCT Filed: Sep. 16, 2013

(86) PCT No.: PCT/EP2013/069094
§ 371 (c)(1),
(2) Date: Mar. 12, 2015

(87) PCT Pub. No.: WO2014/044626
PCT Pub. Date: Mar. 27, 2014

(65) Prior Publication Data
US 2015/0239954 A1    Aug. 27, 2015

(30) Foreign Application Priority Data

Sep. 18, 2012   (CN) .......................... 2012 1 0348296

(51) Int. Cl.
*C07K 14/78*   (2006.01)
*C12P 21/06*   (2006.01)
*C12N 9/62*    (2006.01)

(52) U.S. Cl.
CPC ............... *C07K 14/78* (2013.01); *C12N 9/62* (2013.01); *C12P 21/06* (2013.01); *Y02P 20/52* (2015.11)

(58) Field of Classification Search
None
See application file for complete search history.

(56) References Cited

FOREIGN PATENT DOCUMENTS

| EP | 0353798 A2 | 2/1990 |
| JP | 2505627 62 | 6/1996 |
| WO | 0134646 A2 | 5/2001 |
| WO | 02068623 A2 | 9/2002 |

OTHER PUBLICATIONS

UniProt Database Accession No. A2Q7F7, Jul. 2013, 2 pages.*
International Search Report from corresponding PCT/EP2013/069094, mailed Jun. 26, 2014.
Chomarat et al., "Comparative efficiency of pepsin and proctase for the preparation of bovine skin gelatin", Enzyme and Microbial Technology, vol. 16, No. 9, Sep. 1994 (Sep. 1994), pp. 756-760, XP023679893.
Huang, et al., "Conversion Yield and Molecular Weight Distribution Characteristics of Extracted Gelatins" In: Amman N-Brass, H. & Pouradier, J.: "Photographic Gelatin Proceedings of the Fifth IAG Conference", 1988, XP008168343.
Takahashi, "Aspergillopepsin Ii" in: "Handbook of Proteolytic Enzymes", 2004, XP008168062, ISBN: 0-12-079611-2, vol. I, pp. 221-224.
Brown et al., "Molecular Size and Conformation of Protein Recovered From Chrome Shavings", Journal of the American Leather Chemists Association, vol. 89, Jun. 22, 1994 (Jun. 22, 1994), pp. 215-220, XP009053451.
Olijve et al., "Influence of the Molecular-Weight Distribution of Gelatin on Emulsion Stability", Journal of Colloid and Interface Science, vol. 243, No. 2, Nov. 15, 2001 (Nov. 15, 2001), pp. 476-482, XP055107086.

* cited by examiner

*Primary Examiner* — David J Steadman
(74) *Attorney, Agent, or Firm* — McBee Moore Woodward & Vanik IP, LLC

(57) ABSTRACT

The present invention relates to a process for preparing gelatin comprising a step of incubating a material comprising collagen with an enzyme composition comprising an acid protease which has at least 70% identity to the amino acid sequence of SEQ ID NO:1, and preparing the gelatin. The invention also relates to gelatin obtained by a process as disclosed herein.

8 Claims, 3 Drawing Sheets

SEQUENCE LISTING

```
<160> NUMBER OF SEQ ID NOS: 3

<210> SEQ ID NO 1
<211> LENGTH: 282
<212> TYPE: PRT
<213> ORGANISM: Aspergillus niger

<400> SEQUENCE: 1

Met Lys Phe Ser Thr Ile Leu Thr Gly Ser Leu Phe Ala Thr Ala Ala
1               5                   10                  15

Leu Ala Ala Pro Leu Thr Glu Lys Arg Arg Ala Arg Lys Glu Ala Arg
                20                  25                  30

Ala Ala Gly Lys Arg His Ser Asn Pro Pro Tyr Ile Pro Gly Ser Asp
            35                  40                  45

Lys Glu Ile Leu Lys Leu Asn Gly Thr Ser Asn Glu Asp Tyr Ser Ser
50                  55                  60

Asn Trp Ala Gly Ala Val Leu Ile Gly Asp Gly Tyr Thr Lys Val Thr
65                  70                  75                  80

Gly Glu Phe Thr Val Pro Ser Val Ser Ala Gly Ser Ser Ser Ser Ser
                85                  90                  95

Gly Tyr Gly Gly Gly Tyr Gly Tyr Tyr Lys Asn Lys Arg Gln Ser Glu
            100                 105                 110

Glu Tyr Cys Ala Ser Ala Trp Val Gly Ile Asp Gly Asp Thr Cys Glu
        115                 120                 125

Thr Ala Ile Leu Gln Thr Gly Val Asp Phe Cys Tyr Glu Asp Gly Gln
    130                 135                 140

Thr Ser Tyr Asp Ala Trp Tyr Glu Trp Tyr Pro Asp Tyr Ala Tyr Asp
145                 150                 155                 160

Phe Asn Asp Ile Thr Ile Ser Glu Gly Asp Thr Ile Lys Val Thr Val
                165                 170                 175
```

```
Glu Ala Thr Ser Lys Ser Ser Gly Ser Ala Thr Val Glu Asn Leu Thr
            180                 185                 190

Thr Gly Gln Ser Val Thr His Thr Phe Ser Gly Asn Val Glu Gly Asp
        195                 200                 205

Leu Cys Glu Thr Asn Ala Glu Trp Ile Val Glu Asp Phe Glu Ser Gly
    210                 215                 220

Asp Ser Leu Val Ala Phe Ala Asp Phe Gly Ser Val Thr Phe Thr Asn
225                 230                 235                 240

Ala Glu Ala Thr Ser Asp Gly Ser Thr Val Gly Pro Ser Asp Ala Thr
            245                 250                 255

Val Met Asp Ile Glu Gln Asp Gly Thr Val Leu Thr Glu Thr Ser Val
        260                 265                 270

Ser Gly Asp Ser Val Thr Val Thr Tyr Val
        275                 280

<210> SEQ ID NO 2
<211> LENGTH: 6
<212> TYPE: PRT
<213> ORGANISM: Artificial Sequence
<220> FEATURE:
<223> OTHER INFORMATION: Xaa in the Edans-Dabcyl substrate can be any
      amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Ala Ala Xaa Ala Ala Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Edans-Dabcyl substrate

<400> SEQUENCE: 3

Ala Ala His Ala Ala Lys
1               5
```

PROCESS FOR THE PREPARATION OF GELATIN

CROSS REFERENCE TO RELATED APPLICATIONS

Figure 1:
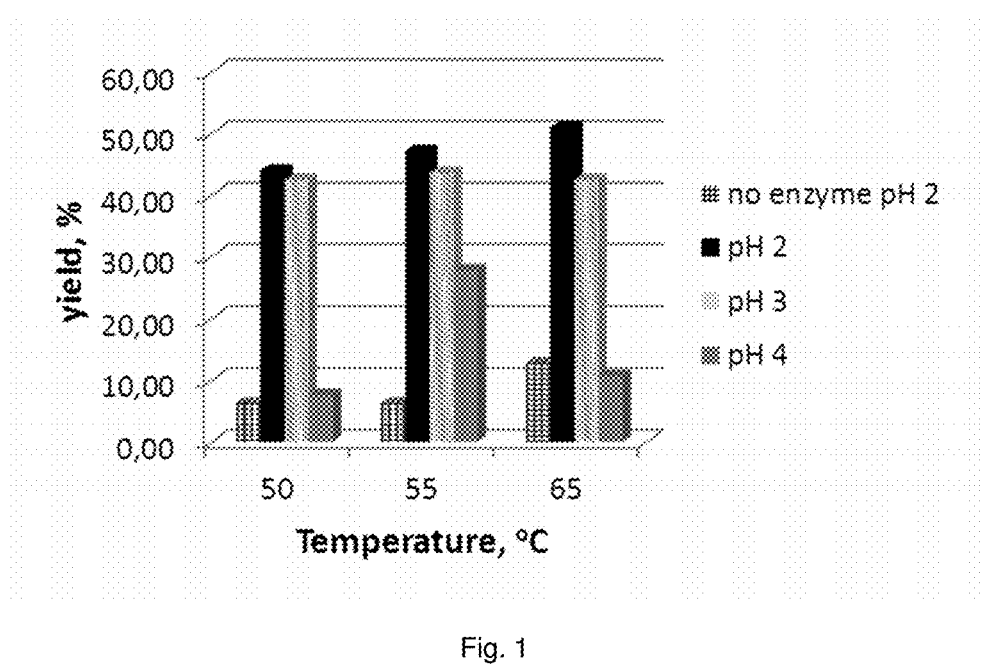

This application is a §371 National Stage Application of PCT/EP2013/069094, filed Sep. 16, 2013, which claims priority to CN 201210348296.7, filed Sep. 18, 2012.

BACKGROUND

Field of the Invention

The present invention belongs to a process for the preparation of gelatine by enzymatic treatment of collagen.

Description of Related Art

Gelatin is a mixture of peptides and proteins obtained by solubilizing collagen. Collagen is predominantly extracted from various animal by-products such as bones and skin using an alkaline or acid pretreatment.

Traditionally gelatin may be extracted from collagen using hot water in a multi-stage extraction to solubilize collagen into gelatin. Typically, three temperature stages of hot water extraction can be used: (1) 50-55° C.; (2) 60-65° C.; and (3) 70-75° C. The higher the water temperature used in the extraction, the higher collagen solubilization is obtained, but lower gelatin strength. Collagen comprises three polypeptide strands, so-called alpha strands (alpha, alpha 1 and alpha 2) and during extraction these collagen peptides are solubilized. After solubilization further treatments may be applied to the gelatin (solubilized collagen), such as filtration, clarification, and drying.

Disadvantages of extracting gelatin using hot water is that large volumes of water are required and a long time is needed for the liming and extraction process.

As an alternative, enzymatic processes for extracting gelatin from collagen have been described. The enzymes are generally used to either improve or replace a pretreatment step in the gelatin process, such as liming, or to increase the yield gelatin during hot water extraction at a lower temperature.

CN102051130 compares the use of an acid protease, pepsin, and several neutral proteases for the extraction of gelatin from defatted demineralized bones. Disadvantages of the processes disclosed in CN102051130 are that a high amount of water was still needed in the gelatin extraction and that an extra heat step was applied to obtain a high yield of gelatin.

CN102329843 discloses the use of an acid protease from *A. niger* for the extraction of gelatin from bone collagen, wherein the enzymatic reaction needed to be carefully controlled to prevent overreaction of the enzyme.

A disadvantage of enzymatic methods for gelatin extraction known in the art is the non-specific proteolytic cleavage of collagen. The broad spectrum proteases used, generate, unless carefully controlled, small protein fragments and therefore lower the gelatin quality.

The aim of the present invention is an improved process for enzymatically extracting gelatin wherein a high quality of the gelatin is obtained at a high yield.

SUMMARY

The present disclosure relates to a process for preparing gelatin comprising a step of incubating a material comprising collagen with an enzyme composition comprising an acid protease which has at least 70% identity to SEQ ID NO:1, and preparing the gelatin.

Surprisingly it was found that during the step of incubating the material comprising collagen with an enzyme composition comprising the acid protease as disclosed herein, the yield of gelatin was higher gelatin obtained with enzymatic processes known in the art while at the same time maintaining a very good quality of gelatin. A high yield as used herein is a yield of at least 60 wt %, or at least 70, or 75 wt % and a good quality is a gelatin with a Bloom value of at least 200, such as at least 240, or at least 260. These high yield values were found in the step of incubating the collagen material with the acid protease without further extraction steps such as a heat treatment. Since these further extraction steps can be omitted, the process for preparing gelatin as disclosed herein advantageously can reduce production costs.

In another embodiment the present disclosure relates to gelatin having at least 10 wt/wt % of peptides having a size of 70 to 90 kDa relative to the weight of alpha peptides of collagen.

BREIF DESCRIPTION OF THE DRAWINGS

Figure 2:
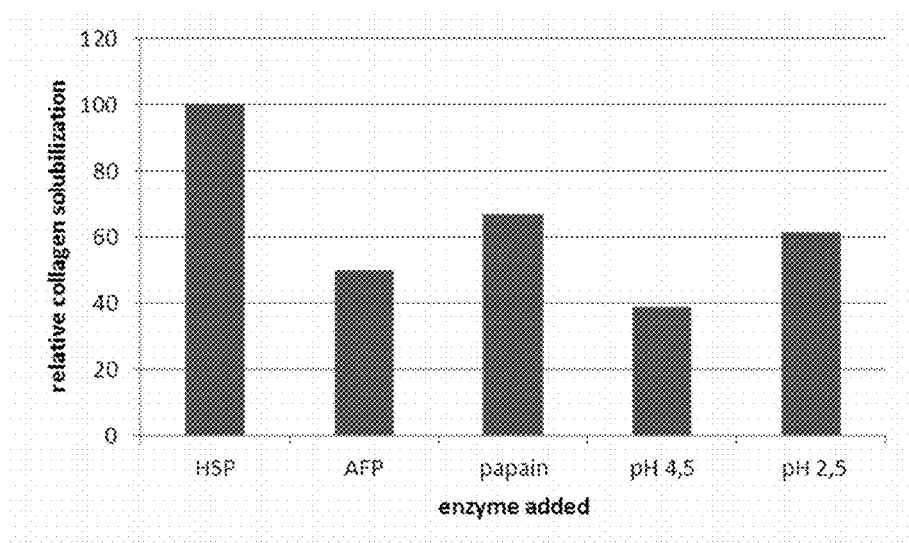
Figure 3:
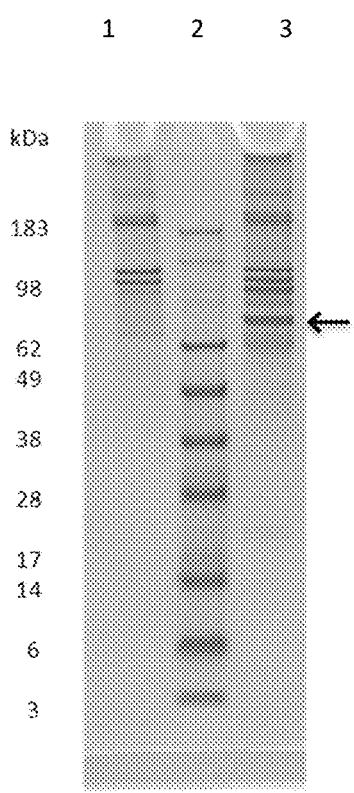

FIGS. 1-3 depict embodiments of the instant disclosure.

DETAILED DESCRIPTION OF A PREFERRED EMBODIMENT

The present invention relates to a process for preparing gelatin comprising a step of incubating a material comprising collagen with an enzyme composition comprising an acid protease which has at least 70% identity to amino acid sequence of SEQ ID NO:1, and preparing the gelatin.

An acid protease in a process as used herein is a protease having a pH optimum at acid pH values, such as between 1 and 6, or between 2 and 5, or between 3 and 4.

The acid protease in a process as disclosed herein was advantageously used since it resulted in a gelatin with a high bloom value and good gelling properties. Compared to known proteases the acid protease used in a process as disclosed herein appeared to cleave the collagen into larger fragments than protease compositions known in the art.

The acid protease may be an enzyme having a preference to cleave a protein or peptide at a certain amino acid position in the protein or peptide. The acid protease may for instance be a histidine specific protease. It was found that when a histidine specific protease was used in a protease as disclosed herein, a high quality of gelatin was obtained.

An acid protease used in a process as disclosed herein is not a broad spectrum protease.

An enzyme composition advantageously comprises an acid protease wherein the acid protease comprises at least 80% by weight of proteins in the enzyme composition, such as at least 85, 90, 95, 98 or 99% by weight of the proteins in the enzyme composition. It was found that an enzyme composition comprising at least 80% by weight of proteins of an acid protease resulted in a good quality of gelatin. A good quality gelatin prepared by a process as disclosed herein comprises at least 10 wt/wt % of a protein having a size of 70 to 90 kDa relative to the weight of alpha peptides of collagen in the gelatin.

Hence the enzyme composition in a process as disclosed herein comprises an acid protease in pure form.

The acid protease may have at least 75, 80, 85, 90, 92, 95, 98, 99 or 100 % identity with the amino acid sequence of SEQ ID NO: 1, or may comprise SEQ ID NO: 1.

The acid protease may be derived from any suitable microorganism, such as from fungi from the genus *Rasamsonia*, *Penicillium* or *Aspergillus*. Preferably the acid protease is derived from the species *Rasamsonis emersonii*, *Penicillium chrysogenum*, *Aspergillus oryzae* or *Aspergillus niger*.

Incubating a material comprising collagen with an enzyme composition comprising an acid protease may be performed at a suitable temperature of between 40 and 65 degrees Celsius, such as between 45 and 60 degrees Celsius, such as between 50 and 59 degrees Celsius, or between 52 and 58 degrees Celsius.

The incubation of the material comprising collagen with the enzyme composition may be performed at a pH of between 1.0 and 4.5, such as a pH of between 1.5 and 4, such as a pH of between 2.0 and 3.5.

It was found that a process for preparing gelatin as disclosed herein could be performed during a shorter period of time as compared to hot water, acid or alkaline processes, which is of great economical interest. Incubating a material comprising collagen with an enzyme composition comprising an acid protease may be performed during a period of between 0.5 to 10 hrs, such as between 1 and 8 hrs or between 2 and 6 hrs.

Preparing gelatin in a process as disclosed herein comprises solubilizing collagen. Solubilizing collagen involves partial hydrolysis or cleavage of molecular (eg. hydrogen) between individual collagen strands or peptides. It was found that by incubating collagen with acid protease in a process as disclosed herein a higher amount of collagen is solubilized as compared to the amount of solubilized collagen obtained with acid proteases known in the art. A process for preparing gelatin as disclosed herein may further comprise separating solubilized collagen from insoluble collagen.

The process for preparing gelatin may comprise a further step of drying the gelatin.

In one embodiment the present disclosure relates to gelatin comprising at least 10 wt/wt % of a peptide having a size of 70 to 90 kDa relative to the weight of alpha peptides of collagen in the gelatin. The gelatin preferably comprises at least an amount of 10 to 90 or at least 20 to 80 or at least 30 to 70 wt/wt % of peptides having a size of 70 to 90 kDa relative to the weight of alpha peptides of collagen. The peptide may have a size of between 72 to 88 kDa, or between 74 and 86 kDa, such as between 76 to 84 kDa The present disclosure also relates to a process for preparing gelatin comprising at least 10 wt/wt % of a protein having a size of 70 to 90 kDa relative to the weight of alpha peptides of collagen in the gelatin as further defined herein above.

In one embodiment, the present disclosure also relates to gelatin obtainable by a process as disclosed herein.

Definitions

The internationally recognized schemes for the classification and nomenclature of enzymes from IUMB include proteases. The system categorises the proteases into endo- and exoproteases. An endoprotease is defined herein as an enzyme that hydrolyses peptide bonds in a polypeptide in an endo-fashion and belongs to the group EC 3.4. The endoproteases are divided into sub-subclasses on the basis of catalytic mechanism. There are sub-subclasses of serine endoproteases (EC 3.4.21), cysteine endoproteases (EC 3.4.22), aspartic endoproteases (EC 3.4.23), metalloendoproteases (EC 3.4.24) and threonine endoproteases (EC 3.4.25).

Sequence identity is herein defined as a relationship between two or more amino acid (polypeptide or protein) sequences, as determined by comparing the sequences. Usually, sequence identities or similarities are compared over the whole length of the sequences compared. In the art, "identity" also means the degree of sequence relatedness between amino acid sequences, as the case may be, as determined by the match between strings of such sequences.

Methods to determine identity are designed to give the largest match between the sequences tested. Methods to determine identity and similarity are codified in publicly available computer programs. Preferred computer program methods to determine identity and similarity between two sequences include BLASTP, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extension 1, Blosum 62 matrix.

Material comprising collagen may be any substance containing collagen, such as animal bone or skin, but may also be extracted or pure collagen. Collagen comprises strands or peptides comprising alpha peptides (alpha, alpha 1 and alpha 2).

Gelatine is a mixture or peptides and proteins and is extracted from collagen, and may also be indicated as collagen hydrolysate of collagen peptide.

A peptide is defined herein as a chain of at least two amino acids that are linked through peptide bonds. The wording peptide may also be used herein to indicate a polypeptide.

A polypeptide is a chain containing at least 30 amino acid residues.

A protein consists of one or more polypeptides folded into a globular or fibrous form.

A histidine specific protease is a protease having a preference for cleaving a peptide or protein at a place where there is a histidine residue in a peptide or protein. Determination of the preference of an enzyme to cleave peptide bonds involving a C-terminal histidine residue is carried out by LC-MC/MC using a Edans Dabcyl substrate, such as disclosed in the Materials and Methods section.

A protease having a broad spectrum of activity does not show a preference for a specific amino acid for cleaving a protein or peptide.

FIG. 1: The yield of soluble collagen after incubation with Aspergillopepsin II at pH 2, 3, and 4 and a temperature of 50, 55 and 65 degrees Celsius.

FIG. 2: The yield of soluble collagen from bone material obtained with Aspergillpepsin I (AFP) at pH 2.5 and papain at pH 4.5 relative to the yield obtained with Aspergillopepsin II (HSP) at pH 2.5. For comparison, the yield of collagen solubilization without enzyme addition is shown at pH 4.5 and pH 2.5.

FIG. 3: SDS-PAGE analysis of the collagen fragments generated by the action of Aspergillopepsin II. Lanes 1 to 3 (from left to right): Lane1-type I collagen incubated at 50° C. for 4 hours at pH 4.5 without enzyme addition; lane 2—SeeBluePlus2 molecular weight marker; lane 3—type I collagen incubated with Aspergillopepsin II at 50° C. and pH 4.5 for 4 hours. The arrow indicates a peptide fragment of approximately 80 kDa.

Materials And Methods

Production of aspergillopepsin II

The gene for aspergillopepsin II (An01g00530; protein sequence SEQ ID NO: 1) was over-expressed in an *A. niger* host using methods such as described in WO 98/46772. WO 98/46772 discloses how to select for transformants on agar plates containing acetamide, and to select targeted multicopy integrants. *A. niger* transformants containing multiple copies of the expression cassette were selected for further generation of sample material. The transformed *A. niger* strain was fermented in a modified CSM-fermentation medium, pH 6.2 (40 g/l Maltose, 30 g/l Bacto-soytone, 70 g/l Sodium citrate tribasic dihydrate, 15 g/l $(NH_4)_2SO_4$ 1 g/l $NaH_2PO_4*2H_2O$, 1 g/l $MgSO_4*7H_2O$, 1 g/l L-Arg, 0.25 ml/l Clerol Antifoam). The culture broth obtained was filtered, sterile filtered and then concentrated by ultrafiltration. Chromatography was carried out by applying the enzyme to a Q-sepharose FF XK 26/20 column in 50 mmol/l Na-acetate pH 5.6, followed by elution with a salt gradient. The presence of the aspergillopepsin II protein in the various fractions was quantified by judging the intensity of coloured protein bands after 4-12% SDS-PAGE (NuPAGE Bis-Tris Gel, Invitrogen).

Determination of Aspergillopepsin II Protease Activity (HPU)

20.0 g haemoglobin from bovine blood (Sigma product H2625) was suspended in approximately 700 mL water by stirring for 10 minutes at room temperature. After the addition of 3.73 g potassium chloride (KCl) the pH was adjusted to 1.75 with 0.5 mol/L hydrochloric acid. The volume of the haemoglobin suspension was adjusted to 1 L with water. The pH was checked again and adjusted to pH 1.75.

Enzyme solutions were prepared by dissolving purified aspergillopepsin II produced as disclosed above in a KCl/HCl buffer containing 3.73 g/l KCl adjusted to pH 1.75 with 2.0 mol/L HCl. To test aspergillopepsin II activity, 5 ml of the haemoglobin solution was heated at 40° C. and subsequently 1 mL enzyme solution with an activity between 5 and 25 Histidine Protease Units (HPU/mL) was added to start the reaction. After 30 minutes the reaction was stopped by adding 5 mL trichloro acetic acid solution (140 g/L) to precipitate larger peptide fragments. A blank measurement was done by adding 1.0 mL enzyme sample to a mixture of 5 mL haemoglobin solution and 5 mL trichloro acetic acid solution. The tubes were incubated at 40° C. for 30 minutes to complete the precipitation. After centrifugation, the optical density of the clear supernatant containing small peptides was measured at 275 nm. The result was compared to an L-tyrosine solution of 1.1 µg/mL.

One HPU is the amount of enzyme that hydrolyzes an amount of haemoglobin per minute, giving a solution with an optical density at 275 nm equal to the optical density of a solution containing 1.10 µg L-tyrosine per mL in 0.1 mol/L HCl solution. Conditions of the test are: pH 1.75, temperature 40 degrees Celsius, haemoglobin concentration during incubation 16.7 g/L.

$$\text{Activity(HPU/mL)} = (OD_{sample} - OD_{blank}/S) \times 11/30$$

Where:
$OD_{sample}$: Optical density of the sample filtrate (275 nm)
$OD_{blank}$: Optical density of the sample blank filtrate (275 nm)
S: OD of a L-tyrosine standard solution of 1.1 µg/mL (mL/µg)
30: incubation time (minutes)
11: total volume reaction mixture (mL)

Specificity of Aspergillopepsin II for Cleaving Peptide Bonds Involving Histidine The cleavage preference of aspergillopepsin II was tested using an E(Edans)-AAXAAK-(Dabcyl)-$NH_2$ (SEQ ID NO: 2) fluorescent substrate kit with "A" representing alanine residues and "X" the 19 different individual amino acid residues as specified by their one-letter code. Dabcyl quenches the Edans fluorescence when the substrate is intact and no longer quenches the Edans fluorescence when the substrate is cleaved. The substrate is therefore called a Fluorescence resonance energy transfer (FRET) peptide. Substrate stock solutions were prepared in DMSO in 5 mM concentration. The reaction mixture contained: 195 microliters of either 100 mM Na-acetate buffer, pH 4.0 or 100 mM Tris-HCl buffer, pH 7.0 to which 2 microliters substrate stock solution and 5 microliters aspergillopepsin II (0.25 mg/ml in 50 mM Na-acetate, pH 5.6) were added. The reaction mixture was incubated in Tecan equipment (Mannedorf, Switzerland) at 37° C. for 60 min ($\lambda_{ex}$=340nm, $\lambda_{em}$=485 nm). The enzyme activity was determined in relative fluorescent units (rfu) per minute per mg of protein. Among the various E(Edans)-AAXAAK-(Dabsyl)-$NH_2$ (SEQ ID NO: 2) substrates tested at pH 4, substrate E(Edans)-AAHisAAK-(Dabsyl)-$NH_2$ (SEQ ID NO:3) yields the highest rfu value for aspergillopepsin II, which means a preference for cleaving substrate E(Edans)-AAHisAAK-(Dabsyl)-$NH_2$(SEQ ID NO:3), i.e. when position X is histidine.

EXAMPLES

Example 1

Optimal Conditions for Collagen Solubilization by Aspergillopepsin II

Insoluble collagen type I, from bovine Achilles tendons was obtained from Sigma-Aldrich Chemie GmbH. A series of 2% (w/v) collagen suspensions in distilled water were prepared in a range of pH from 2 to 4. The pH was adjusted during stirring of the suspension with addition of 1N sulfuric acid. 1.5% (v/w on dry weight collagen) Aspergillopepsin II enzyme (500 HPU/ml) was added to the collagen suspension. The collagen was incubated for 1 hour at set temperatures, varying between 50 to 65° C., in a shaking water bath. The reaction was stopped by removing samples and raising the pH to 7 with 1M sodium hydroxide under stirring. Subsequently, the suspension was filtered through Whatman filter paper to remove the solid residue. The protein content of the solubilized collagen material was measured with Kjeldhal analysis of total nitrogen determination. Collagen solubilization without enzyme addition was only tested at pH 2. The results in FIG. 1 show that at pH 2-3 a higher amount of collagen is solubilized than at pH 4 at all temperatures tested. At 65° C. solubilization of collagen without enzyme addition at pH 2 was higher than at 50 and 55° C.

Example 2

Quality of Gelatin from Collagen Solubilized with Aspergillopepsin II and Pepsin Insoluble collagen type I, from bovine Achilles tendons was obtained from Sigma-Aldrich Chemie GmbH. A series of 4% (w/v) collagen suspensions in distilled water were prepared at pH 2.5 and pH 4.5. The pH was adjusted during stirring of the suspension with addition of 1N sulfuric acid. Either 0.1% (v/w on dry collagen) Aspergillopepsin II (500 HPU/ml) or 0.1% (v/w on dry weight collagen) pepsin from porcine gastric mucosa (Sigma-Aldrich, 500 U/ml) was added to the collagen suspension. The collagen suspension was incubated at 50° C. in a shaking water bath for 4 hours. The reaction was stopped by removing the samples from the suspension and raising the pH to 7 with 1M sodium hydroxide. Subsequently, the samples were filtered through Whatman filter paper to remove the solid residue at temperature around 40° C. (in order to prevent gel formation).

The protein content (yield) of the solubilized collagen material was measured as percent of total solids using a refractometer (pocket refractometer ATAGO Tokyo) with a reference line of pure bovine gelatin (Sigma-Aldrich).

Subsequently, the collagen samples solubilized with Aspergillopepsin II and pepsin, were dried in a vacuum oven (Heraeus Instruments) at 40° C. and the concentrated gelatins were redissolved in warm water to the desired protein concentration. A 4% protein gel was prepared samples to compare the gel strength of the two gelatins obtained.

In addition, two other samples were prepared: one 6.6% protein gel from the Aspergillopepsin II treated collagen and a 6.6% protein gel from the commercial bovine skin gelatin (Sigma-Aldrich).

After cooling down to room temperature, the samples were stored at 8-10° C. overnight for gel setting. The gel strength (as compression in grams) for the 4% gels and the Bloom value for the 6.6% gels were measured with a texture analyzer, TA.XT PLUS (stable Micro systems) according to the Bloom method.

Table 1 shows that the yield of gelatin (soluble collagen) obtained after collagen treatment with aspergillopepsin II was about 3 times higher than with pepsin. In addition gelatin obtained with aspergillopepsin II had an increased gel strength compared to the gelatin obtained with pepsin. The gelatin obtained after treatment with aspergillopepsin II had a similar gel strength (Bloom value) as the commercially available gelatin.

The material was then centrifuged at 4000 rpm (approximately 2800 g) for 10 minutes and the supernatant was collected. Water was added to the residue at a ratio of 7:1 and gelatin was extracted for a second time with 0.1% (g/g wet bone) Aspegillopepsin II. The second extraction was carried out at 53° C. for 4 hours followed by centrifugation at 4000 rpm (~2800 g) for 10 minutes.

The yield was calculated after centrifugation based on the total solid content measured by the refractometer. The yield from the first extraction was between 50-62%; and the yield of the second extraction was between 15-27%.

The supernatants from the two enzymatic extractions were combined and the pH was adjusted to 6 to inactivate the enzyme. Subsequently the solution was filtered through Diatomite and the filtered solution was subjected to vacuum concentration at 70° C. until the total solids content was approximately 6.6% as measured using a refractometer.

The Bloom value of the gelatin obtained was measured using a texture analyzer as described above (For the method of determining gel strength, please refer to food additive gelatine in GB6783-94 in national standard of People's Republic of China which was enforced dated from 1 Oct. 1995).

The bloom value of the enzyme treated bone material was about 240 g.

The results in Example 3 show that a good quality (Bloom value of 240) gelatin can be obtained using Aspergillopepsin II after collagen extraction from bones.

TABLE 1

Comparison of the yield and the gel strength of the gelatins prepared with Aspergillopepsin II and pepsin and commercial gelatin from Bovine skin.

| Enzyme | Dosage (%,v/w) | pH | T (° C.) | Time, h | Yield Solubilized protein % | Gel strength (4%) g | Bloom (6.6%) g |
|---|---|---|---|---|---|---|---|
| No enzyme | 0 | 2.5 | 50 | 4 | — | — | — |
| Aspergillopepsin II | 0.1 | 2.5 | 50 | 4 | 75 | 127 | 295 |
| Pepsin | 0.1 | 2.5 | 50 | 4 | 32 | 85 | — |
| Commercial gelatin (bovine skin) | — | — | — | — | — | 130 | 250-300 |

Example 3

Bloom Value of Gelatin Extracted from Bovine Bone Material Using Aspergillopepsin II 100 g bovine bone slices were treated with 4%-6% hydrochloric acid to remove the minerals. The concentration of hydrochloric acid was gradually decreased to 0.5% in immersion. The demineralization process was stopped once the concentration of hydrolchloric acid remained unchanged.

The pH value was adjusted to be 4.2-4.4 by adding 5-15% sodium hydroxide solution.

The bone slices were washed with water to clean the remaining impurities on the bone surface and then the bones were comminuted to less than 1-5 mm size.

Further water was added to the pretreated bone particles to a ratio of 1:7 wet bone to water. A 0.1% (g/g wet bone) of Aspergillopepsin II was added and the extraction was carried out at 53° C. for 4 hours. The pH during the extraction process was kept constant at about 4.2 by addition of sodium hydroxide.

Example 4

Yield of Gelatin Extraction from Bone Material Using Various Enzymes

Bone slices were acidulated with 6% (w/w) hydrochloric acid solution every 12 hours for 3 days to remove minerals. At the end of the demineralization process the bones were washed with water and the pH adjusted to 6 with 15% sodium hydroxide solution. The demineralized bones were milled to a diameter <5 mm. Water was added to the pretreated bones to a ratio 7:1. Prior to enzyme addition the pH was adjusted to a desired value with 20% phosphoric acid solution.

To test the yield of gelatin extraction (collagen solubilization) collagen was incubated at 50° C. for 4 hours with the following enzymes at a dosage of 0.02% (v/w enzyme to wet bones), Apergillopepsin II (500 HPU/ml) at pH 2.5,
Aspergillopepsin I (Validase® AFP 1000 L, DSM product, 1000 SAPU/g; EC. 3. 4.23.18) at pH 2.5, and papain (Collupulin® L, DSM product of 80-90 U/ml) at pH 4.5; and a collagen sample without addition of enzyme at pH 2.5; and a collagen sample without addition of enzyme at 4.5.

The enzyme reaction was stopped by adjusting the pH to 6 with sodium hydroxide and subsequently the material was filtered through filter paper.

The yield of collagen solubilization (total solids solubilized) was measured using a refractometer. FIG. 2 shows that collagen incubation with Aspergillopepsin II results in the highest yield of soluble collagen (gelatin).

Example 5

Specific Cleavage of Collagen by Aspergillopepsin II

Insoluble collagen type I, from bovine Achilles tendons was obtained from Sigma-Aldrich Chemie GmbH. A series of 4% (w/v) collagen suspensions in distilled water were prepared at pH 4.5. The pH was adjusted during stirring of the suspension with addition of 1N sulfuric acid. Either 0.1% (v/w on dry collagen) Aspergillopepsin II enzyme (500 U/ml), papain (Collupulin® L, DSM product of 80-90 U/ml) or no enzyme was added to the collagen suspension. The collagen suspensions were incubated at 50° C. in a shaking water bath for 4 hours. The reaction was stopped by removing the samples from the suspension and raising the pH to 7 with 1 M sodium hydroxide. Subsequently, the suspension was filtered through Whatman filter paper to remove the solid residue at a temperature around 40° C. (in order to prevent gel formation).

A similar experiment as described herein at pH 4.5 was carried out at pH 2.5 using Aspergillopepsin II enzyme (500 U/ml) and pepsin (Sigma-Aldrich, 500 U/ml).

The peptide products present in the solubilized material were analyzed by SDS-PAGE using the method of Laemmli. Samples were mixed with NuPage LDL sample buffer (Invitrogen Corp.), reducing agent and heated at 70° C. for 10 min. 10 µl samples were subsequently loaded on the 4-12% Bis-Tris gel (Invitrogen) using NuPage MES SDS running buffer. As a molecular weight marker, SeeBlue Plus2 (Invitrogen) was used. The gel was stained with Coomassie brilliant blue. The intensity of the protein bands was determined using an OptiGO scanner (Isogen life sciences) with Totallab analysis software (Isogen life sciences) and the weight of the proteins was calculated.

FIG. 3 is an example of an SDS gel of solubilized collagen obtained with aspergillopepsin II at pH 4.5. The picture shows a pronounced peptide band corresponding to a size of about 80 kDa. A pronounced peptide band of about 80 kDa was also found in solubilized collagen incubated with aspergillopepsin at pH 2.5.

This peptide of about 80 kDa was not found or barely visible after incubation with papain or pepsin (results not shown).

The invention claimed is:

1. A process for preparing gelatin comprising:
   incubating a material comprising collagen with an enzyme composition comprising an acid protease to solubilize the collagen, wherein the acid protease has aspergillopepsin II protease activity and comprises an amino acid sequence which has at least 95% sequence identity to the amino acid sequence of SEQ ID NO: 1, and
   preparing gelatin from the solubilized collagen,
   wherein the acid protease comprises at least 99% by weight of proteins in the enzyme composition, and wherein the yield of gelatin is at least 60% by weight of the material comprising collagen and the gelatin has a Bloom value of at least 200.

2. The process according to claim 1, wherein the incubating is performed at a temperature of between 40 and 65 degrees Celsius.

3. The process according to claim 1, wherein the incubating is performed at a pH of between 1.5 and 4.5.

4. The process according to claim 1 wherein the incubating is performed during a period of 1 to 10 hrs.

5. The process according to claim 1 wherein the acid protease is derived from an *Aspergillus niger* species.

6. The process according to claim 1, further comprising separating solubilized collagen from insoluble collagen.

7. The process according to claim 1 further comprising drying the gelatin.

8. The process according to claim 1, wherein the incubating is performed at a temperature of between 40 and 65 degrees Celsius, at a pH of between 1.5 and 4.5, and for a period of 1 to 10 hrs.

* * * * *